US011033529B2

(12) United States Patent
Weiser et al.

(10) Patent No.: US 11,033,529 B2
(45) Date of Patent: Jun. 15, 2021

(54) METHOD OF TREATING NEURODEGENERATIVE DISORDERS

(71) Applicant: Cortice Biosciences, Inc., New York, NY (US)

(72) Inventors: Michael Weiser, New York, NY (US); Jason Stein, New York, NY (US); Donald Picker, Jersey City, NJ (US)

(73) Assignee: Cortice Biosciences, Inc., New York, NY (US)

( * ) Notice: Subject to any disclaimer, the term of this patent is extended or adjusted under 35 U.S.C. 154(b) by 0 days.

(21) Appl. No.: 15/624,263

(22) Filed: Jun. 15, 2017

(65) Prior Publication Data

US 2017/0281592 A1   Oct. 5, 2017

Related U.S. Application Data

(63) Continuation of application No. 14/902,190, filed as application No. PCT/US2014/045185 on Jul. 2, 2014, now abandoned.

(60) Provisional application No. 61/935,607, filed on Feb. 4, 2014, provisional application No. 61/842,358, filed on Jul. 2, 2013.

(51) Int. Cl.
*A61K 31/357* (2006.01)
*A61P 25/28* (2006.01)

(52) U.S. Cl.
CPC ............ *A61K 31/357* (2013.01); *A61P 25/28* (2018.01)

(58) Field of Classification Search
CPC ........ A61K 31/357; A61P 25/14; A61P 25/16; A61P 25/28; A61P 25/00
See application file for complete search history.

(56) References Cited

U.S. PATENT DOCUMENTS

| 8,273,789 B2 * | 9/2012 | McChesney | ......... | C07D 493/06 514/453 |
| 2009/0306014 A1 | 12/2009 | Ballatore et al. | | |
| 2011/0118299 A1 | 5/2011 | Lovell et al. | | |
| 2013/0022668 A1 | 1/2013 | McChesney et al. | | |

FOREIGN PATENT DOCUMENTS

| WO | 2008106621 A1 | 9/2008 |
| WO | 2011028571 A1 | 3/2011 |
| WO | 2013096870 A1 | 6/2013 |

OTHER PUBLICATIONS

Wong et al., "Bridging the Gap between Preclinical and Clinical Studies Using Pharmacokinetic-Pharmacodynamic Modeling: An Analysis of GDC-0973, a MEK Inhibitor", Clin. Cancer Res., vol. 18, pp. 3090-3099 (2012).
International Search Report for PCT/US2014/045185 dated Oct. 31, 2014.
Ballatore et al., "Microtubule Stabilizing Agents as Potential Treatment for Alzheimer's Disease and Related Neurodegenerative Tauopathies", J Med Chem., vol. 55, No. 21, pp. 8979-8996 (2012).
Office Action issued in Chilean Application No. 3668-2015 dated Feb. 15, 2017.
International Patent Application No. PCT/US2014/045185 Written Opinion dated Oct. 31, 2014, 10 pages.
Israeli Patent Application No. 242979 Office Action dated May 24, 2018, 3 pages.
Japanese Patent Application No. 2016-524338 Notice of Reasons for Rejection dated Mar. 28, 2018, 5 pages.
Chilean Patent Application No. 3668-2015 Office Action dated Sep. 5, 2017 (5 pages).
European Patent Application No. 14819753.6 Communication dated Mar. 2, 2018 (6 pages).
Examination report dated Sep. 26, 2018 for Australian Application. No. 2014284304, 4 pages.
Office Action dated Oct. 22, 2018 for Mexican Application No. MX/a/2015/016951, 12 pages.
Office Action dated Nov. 26, 2018 for Japanese Application No. 2016-524338, 8 pages.
Examination report dated Aug. 22, 2019 for Australia Application No. 2014284304, 4 pages.
Office action dated Jun. 23, 2019 for Israel Patent Application No. 242979, 3 pages.
Office action dated Jun. 19, 2019 for Mexican Patent Application No. MX/a/2015/016951, 6 pages.
Indian First Examination Report dated Jan. 11, 2019; 3 pages.
Israel Office Action for IL Patent Application No. 242979; dated Oct. 21, 2020; 3 pages.
Annex to the Communication from the European Patent Office for EP 19 169 972.7; dated Sep. 7, 2020; 3 pages.
Communication from the European Patent Office for EP 19 169 972.7; dated Sep. 7, 2020; 2 pages.
Japanese Notice of Reasons for Refusal for JP 2018-183806; dated Aug. 28, 2020; 3 pages.
English translation of Japanese Notice of Reasons for Refusal for JP 2018-183806; dated Aug. 28, 2020; 3 pages.
Office Action issued in Brazil Application No. BR 11 2015 032194 1 dated Oct. 29, 2019.
Office Action issued in Chilean Application No. 3668-2015 dated Nov. 13, 2019.
Office Action issued in European Application No. 19169972.7 dated Jul. 22, 2019.

(Continued)

*Primary Examiner* — My-Chau T. Tran
(74) *Attorney, Agent, or Firm* — Morgan, Lewis & Bockius LLP

(57) ABSTRACT

The present disclosure is directed, at least in part, to disease-modifying treatments for neurodegenerative disorders. In one embodiment, a method of delaying worsening of one or more symptoms and/or progression of a neurodegenerative disorder is provided. In one embodiment, a method of treating or ameliorating one or more symptoms of a neurodegenerative disorder is provided. In one embodiment, the methods of the present invention comprise administering to a subject in need thereof, a compound having the structure of Formula (1a); Formula (1a); and/or a pharmaceutically acceptable salt thereof. In one embodiment, the the compound of (1a) and/or a pharmaceutically acceptable salt thereof is administered in combination with one or more pharmacologically active agents.

13 Claims, No Drawings

(56) References Cited

OTHER PUBLICATIONS

Office Action issued in Indian Application No. 11816/DELNP/2015 dated Jan. 11, 2019.
Office Action issued in New Zealand Application No. 715076 dated Jul. 17, 2020.
Office Action issued in New Zealand Application No. 754926 dated Jul. 17, 2020.
Examination Report dated Jan. 6, 2021 for Australian Patent Application No. 2019271983.
Office action dated Nov. 30, 2020 for Korean Patent Application No. 10-2015-7037141.
Second Examination Report dated Mar. 16, 2021 for New Zealand Patent Application No. 715076.
Second Examination Report dated Mar. 16, 2021 for New Zealand Patent Application No. 754926.
Final Official Action and a Denial of Entry of Amendment both dated Mar. 30, 2021 in Japanese Patent Application No. 2018-183806.

* cited by examiner

METHOD OF TREATING NEURODEGENERATIVE DISORDERS

CROSS-REFERENCE TO RELATED APPLICATIONS

This application is a continuation of U.S. Non-provisional application Ser. No. 14/902,190, filed Dec. 30, 2015, currently, which is the national stage entry of International Patent Application No. PCT/US2014/045185, filed Jul. 2, 2014, which in turn claims priority to, and the benefit of, U.S. Provisional Patent Application Nos. 61/842,358, filed Jul. 2, 2013, and 61/935,607, filed Feb. 4, 2014, all of which are incorporated herein by reference in their entireties.

BACKGROUND OF THE INVENTION

The present invention generally relates to a method of treating or ameliorating one or more symptoms of a neurodegenerative disorders and, more particularly, to a method of treating or ameliorating one or more symptoms of Alzheimer's disease.

BRIEF SUMMARY OF THE INVENTION

In one embodiment there is a method of treating and/or ameliorating one or more symptoms of a neurodegenerative disorder, comprising administering to a subject in need thereof, a compound having the structure of Formula (1):

Formula (1)

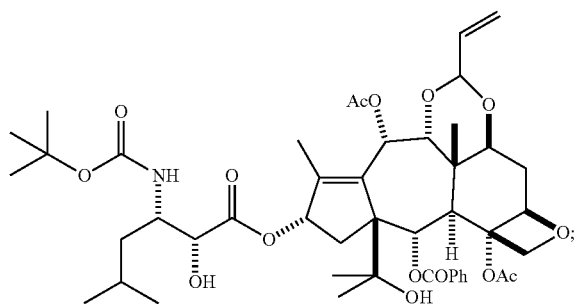

and/or a pharmaceutically acceptable salt thereof at a dose ranging from about 0.001 mg/Kg to about 2000 mg/Kg of body weight or from about 0.001 mg/m$^2$ to about 160 mg/m$^2$.

In one embodiment, the compound of Formula (1) has the structure of Formula (1a):

Formula (1a)

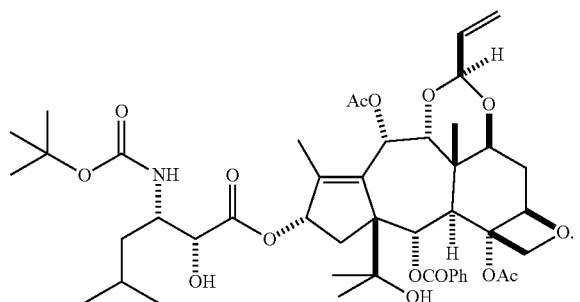

In one embodiment, the compound of Formula (1) has the structure of Formula (1b):

Formula (1b)

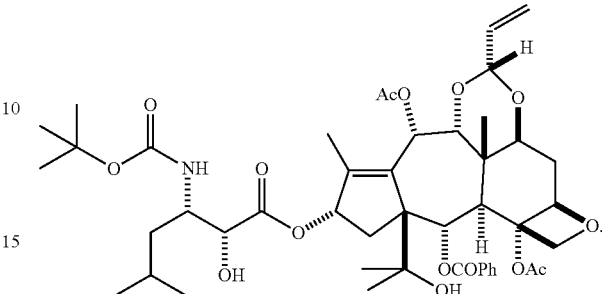

In one embodiment, the compound of Formula (1), (1a), or (1b) and/or the pharmaceutically acceptable salt thereof is administered is administered orally, subcutaneously, intravenously, intramuscularly, intranasally, transdermally or sublingually.

In one embodiment, the neurodegenerative disorder is selected from the group consisting of Alzheimer's disease (AD), Parkinsonian syndromes (PD), Huntington's disease (HD), Prion diseases, cerebral amyloid angiopathy (CAA), and mild cognitive impairment (MCI). In one embodiment, the neurodegenerative disorder is selected from the group consisting of Alzheimer's disease, Pick's disease, corticobasal degeneration, progressive supranuclear palsy and frontotemporoparietal dementia. In one embodiment, the neurodegenerative disorder is selected from the group consisting of Alzheimer's disease, frontotemporal dementias, Parkinson's disease, and polyglutamine diseases, sporadic and familial Alzheimer's disease, Down's syndrome, progressive supranuclear palsy, Huntington's disease, sporadic and familial synucleinopathies, multiple system atrophy, neurodegeneration with brain iron accumulation, neuronal intranuclear inclusion disease, hereditary spastic paraplegias, Charcot-Marie-Tooth disease, and sporadic or hereditary prion disease. In one embodiment, the neurodegenerative disorder is selected from the group consisting of a cognitive disorder, Alzheimer's disease, a neuro-degenerative disorder, age-related dementia, age-induced memory impairment, and movement disorder. In one embodiment, the compound having the structure of Formula (1), (1a) or (1b) and/or a pharmaceutically acceptable salt thereof can be administered in combination with a therapeutically effective amount of another pharmacological agent. In one embodiment, the pharmacological agents that would, in combination with the compounds of the present invention, be most effective in treating or ameliorating one or more symptoms of neurodegenerative disorders include, but are not limited to, antipsychotic drugs, antidepressants, mood-stabilizing drug, and combinations thereof.

DETAILED DESCRIPTION OF THE INVENTION

The present subject matter will now be described more fully hereinafter with reference to representative embodiments. The present subject matter can, however, be embodied in different forms and should not be construed as limited to the embodiments set forth herein. Rather, these embodiments are provided to describe and enable one or skill in the art. Unless otherwise defined, all technical and scientific terms used herein have the same meaning as commonly understood by one of ordinary skill in the art to which the subject matter pertains. All publications, patent applications, patents, and other references mentioned herein are incorporated by reference in their entireties.

I. Neurodegenerative Diseases

Neurodegenerative diseases are characterized by selective and progressive loss of specific populations of neurons, which determines the clinical presentation. The same neuronal populations may be affected in a number of different disorders. Accordingly, neurodegenerative disorders are classified according to the underlying molecular pathology rather than their clinical presentation. The major neurodegenerative diseases can be classified into amyloidoses, tauopathies, α-synucleinopathies and TDP-43 proteinopathies.

The presence of abnormal proteins with specific properties defines the amyloidoses, of which Alzheimer disease (AD) is the most common. Amyloid is a generic name for proteins with common physicochemical properties (e.g., Congo red birefringence) due to abnormal conformation, with cross beta-pleated sheets, which gives the protein a propensity to form fibrils and to aggregate, most often as extracellular deposits in the brain. The amyloidoses are sometimes referred to as beta-fibrilloses to reflect this molecular property. The amyloid protein in AD, Aβ, is derived from a precursor protein, amyloid precursor protein (APP) by regulated intramembranous proteolysis. Deposits of Aβ are not found only in AD, however. Deposits of Aβ are also found in elderly nondemented individuals. As such it is possible to detect Aβ deposits in the brains of living subjects with positron emission tomography, for example, and to assess their chances of developing amyloidoses before clinical manifestation of these diseases. Deposits of Aβ are found in other neurodegenerative disorders, as a function of age and apolipoprotein E ε4 carrier state, which is the major genetic risk factor for AD. Amyloid plaques are often abundant in dementia with Lewy bodies (DLB), familial British dementia (FBD)

Degenerative dementia associated with non-Aβ amyloid deposits include Creutzfeldt-Jacob disease ("CJD"), sporadic CJD, Gerstmann-Straussler-Scheinker syndrome ("GSS"), and tauopathies, which are a class of neurodegenerative diseases associated with the pathological aggregation of the microtubule associated protein, tau, in the human brain. Disorders in which tau pathology is considered to be the major contributing factor to neuro-degeneration are referred to as "primary tauopathies. The most common of the primary tauopathies are 4R tauopathies, which are re associated with both neuronal and glial tau inclusions. The most common of these is argyrophilic grain disease ("∓AGD"), which increases in frequency with age and is detected in about 5% of autopsies of individuals with late onset dementia. Other 4R tauopathies include corticobasal degeneration ("CBD"), progressive supranuclear palsy ("PSP"), Pick's disease ("PiD"), Guam Parkinson dementia complex ("PDC"), and tangle predominant dementia.

Other degenerative disorders associated with non-Aβ amyloid deposits include synucleinopathies, which are characterized by the presence of α-synuclein, which in turn is also the major structural protein in Lewy bodies, the hallmark histopathologic lesion in Parkinson disease ("PD") and dementia with Lewy bodies ("DLB"). PD is a disorder characterized by bradykinesia, tremor and rigidity with gait and balance disorders. Motor deficits in PD are associated with loss of substantia nigra dopaminergic neurons.

Other degenerative disorders include PD with dementia (PDD); multiple system atrophy (MSA), which is a sporadic synucleinopathy characterized by autonomic dysfunction, parkin-sonism and cerebellar ataxia, associated with neurodegeneration of the substantia nigra, basal ganglia, pontine nuclei, interior olivary nucleus and the cerebellum; frontotemporal lobar degeneration (FTLD), a generic term for the group of non-Alzheimer degenerative dementias with focal cortical pathology in frontal and temporal lobes, and encompasses a range of different clinical syndromes—behavioral variant fronto-temporal dementia (FTDbv) progressive nonfluent aphasia (PNFA), semantic dementia (SD) and corticobasal syndrome (CBS); Hippocampal sclerosis (HpScl), which is characterized by neuronal loss in the subiculum and $CA_1$ of the hippocampus; amyotrophic lateral sclerosis (ALS); and frontotemporal lobar degeneration with ubiquitinated inclusions (FTLD-U).

Alzheimer's disease ("AD") is an example of tauopathies, in which tau protein is deposited within neurons in the form of neurofibrillary tangles (NFTs). Tangles are formed by hyperphosphorylation of a microtubule-associated protein known as tau, causing it to aggregate in an insoluble form. These aggregations of hyperphosphorylated tau protein are also referred to as paired helical filaments ("PHF"). The precise mechanism of tangle formation is not completely understood.

II. Compositions

While it is possible for a pharmaceutically active ingredient to be administered alone, it is preferable for it to be present in a pharmaceutical formulation or composition. Accordingly, the compound of Formula (1), (1a), or (1b) or pharmaceutically acceptable salts thereof, are preferably in the form of a pharmaceutical formulation comprising the compound of Formula (1), (1a), or (1b) or pharmaceutically acceptable salts thereof and a pharmaceutically acceptable excipient. The pharmaceutical compositions may take the form of any suitable pharmaceutical formulation including the ones described below.

In one embodiment, the pharmaceutical formulations include those suitable for oral, parenteral (including subcutaneous, intradermal, intramuscular, intravenous, and intraarticular), inhalation (including fine particle dusts or mists which may be generated by means of various types of metered doses, pressurized aerosols, nebulizers or insufflators), rectal and topical (including dermal, transdermal, transmuscosal, buccal, sublingual, and intraocular) administration, although the most suitable route may depend upon, for example, the condition and disorder of the recipient.

The formulations may conveniently be presented in unit dosage form and may be prepared by any of the methods well known in the art of pharmacy. All methods include the step of bringing the active ingredient into association with the carrier which constitutes one or more accessory ingredients. In general the formulations are prepared by uniformly and intimately bringing into association the active ingredient with liquid carriers or finely divided solid carriers or both and then, if necessary, shaping the product into the desired formulation.

In one embodiment, formulations of the present invention that are suitable for oral administration may be presented as discrete units such as capsules, cachets or tablets each containing a predetermined amount of the compound of Formula (1), (1a), or (1b) or pharmaceutically acceptable salts thereof; as a powder or granules; as a solution or a suspension in an aqueous liquid or a non-aqueous liquid; or as an oil-in-water liquid emulsion or a water-in-oil liquid emulsion. The compound of formula (1), (1a), or (1b) or pharmaceutically acceptable salts thereof may also be presented as a bolus, electuary or paste. Various pharmaceutically acceptable carriers and their formulation are described in standard formulation treatises, e.g., Remington: The Science and Practice of Pharmacy, 22nd Edition, 2012, Pharmaceutical Press, edited by Loyd V. Allen.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The present compounds can, for example, be administered in a form suitable for immediate release or extended release. Immediate release or extended release can be achieved by the use of suitable pharmaceutical compositions comprising the present compounds, or, particularly in the cases of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compound of formula (I) or pharmaceutically acceptable salts thereof can also be delivered through the oral cavity by sublingual and/or buccal administration. Molded tablets, compressed tablets or freeze-dried tablets are exemplary forms which may be used. Exemplary compositions include those formulating the present compounds with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPD), hydroxy propyl methyl cellulose (HPMC), sodium carboxy methyl cellulose (SCMC), maleic anhydride copolymer (e.g., Gentrez), and agents to control release such as polyacrylic copolymer (e.g. Carbopol 934). Lubricants, glidants, flavors, coloring agents and stabilizers may also be added for ease of the fabrication and use. Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents, thickening agents and P-glycoprotein (P-gp) inhibitors. The formulations may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use. Extemporaneous injection solutions and suspensions may be prepared from sterile powders, granules and tablets of the kind previously described. Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. In one embodiment, compositions for parenteral administration comprise up to 15% Cremaphor and up to 85% alcohol. In one embodiment, compositions for parenteral administration comprise up to 50% Cremaphor and up to 50% alcohol. In one embodiment, compositions for parenteral administration comprise up to 15% Cremaphor and up to 85% ethanol. In one embodiment, compositions for parenteral administration comprise up to 50% Cremaphor and up to 50% ethanol. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. Excipients that can be included are, for instance, non-toxic auxiliary substances, such as wetting or emulsifying agents, preservatives, and pH buffering agent and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the compound of the invention is delivered in the form of an aerosol spray presentation from a pressurized pack of a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated to contain a powder mix of the compound and a suitable powder base, for example lactose or starch. In one specific, non-limiting example, a compound of the invention is administered as an aerosol from a metered dose valve, through an aerosol adapter also known as an actuator. Optionally, a stabilizer is also included, and/or porous particles for deep lung delivery are included (e.g., see U.S. Pat. No. 6,447,743).

Formulations for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

Preferred unit dosage formulations are those containing an effective dose, as disclosed herein. It should be understood that in addition to the ingredients particularly mentioned above, the formulations of this invention may include other agents conventional in the art having regard to the type of formulation in question, for example those suitable for oral administration may include flavoring agents.

The compound of Formula (1), (1a), or (1b) and/or pharmaceutically acceptable salts thereof are also suitably administered as sustained-release systems. Suitable examples of sustained-release systems of the invention include suitable polymeric materials, for example semipermeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained-release systems may be administered orally; rectally; parenterally; intracisternally; intravaginally; intraperitoneally; topically; for example as a powder, ointment, gel, drop or transdermal patch; bucally; or as an oral or nasal spray.

Preparations for administration can be suitably formulated to give controlled release of compounds of the invention. For example, the pharmaceutical compositions may be in the form of particles comprising one or more of biodegradable polymers, polysaccharide jellifying and/or bioadhesive polymers, amphiphilic polymers, agents capable of modifying the interface properties of the particles of the compound of Formula (1), (1a), or (1b) and/or pharmaceutically acceptable salts thereof. These compositions exhibit certain biocompatibility features which allow a controlled release of the active substance. See U.S. Pat. No. 5,700,486.

The compound of Formula (1), (1a), or (1b) and/or pharmaceutically acceptable salts thereof may be delivered by way of a pump or by continuous subcutaneous infusions, for example, using a mini-pump. An intravenous bag solution may also be employed. The key factor in selecting an appropriate dose is the result obtained, as measured by improvements in one or more symptoms of neurodegenerative disorders of interest, or by other criteria for measuring control or prevention of one or more symptoms of neurodegenerative disorders of interest, as are deemed appropriate by the practitioner. Other controlled release systems are discussed in the review by Langer (Science 249:1527-1533, 1990). In another aspect of the disclosure, compound of Formula (1) and/or pharmaceutically acceptable salts thereof are delivered by way of an implanted pump, described, for example, in U.S. Pat. Nos. 6,436,091; 5,939, 380; and 5,993,414.

Implantable drug infusion devices are used to provide patients with a constant and long term dosage or infusion of a drug or any other therapeutic agent. Essentially such device may be categorized as either active or passive. The compound of Formula (1), (1a), or (1b) and/or pharmaceutically acceptable salts thereof may be formulated as a depot preparation. Such a long active depot formulation can be administered by implantation, for example subcutaneously or intramuscularly; or by intramuscular injection. Thus, for example, the compound of Formula (1), (1a), or (1b) and/or pharmaceutically acceptable salts thereof can be formulated with suitable polymeric or hydrophobic materials, for example as an emulsion in an acceptable oil; or ion exchange resins; or as a sparingly soluble derivatives, for example, as a sparingly soluble salt.

A therapeutically effective amount of the compound of Formula (1), (1a), or (1b) and/or pharmaceutically acceptable salts thereof may be administered as a single pulse dose, as a bolus dose, or as pulse doses administered over time. Thus, in pulse doses, a bolus administration of a compound of the invention is provided, followed by a time period wherein no a compound of the invention is administered to the subject, followed by a second bolus administration. In specific, non-limiting examples, pulse doses of a compound of the invention are administered during the course of a day, during the source of a week, or during the course of a month.

In one embodiment, a therapeutically effective amount of a compound of the invention is administered with a therapeutically effective amount of another pharmacological agent. In one embodiment, the pharmacological agents that would, in combination with the compounds of the present invention, be most effective in treating or ameliorating one or more symptoms of neurodegenerative disorders include, but are not limited to, Razadyne, Exelon, Aricept, Cognex, and Namenda. In one embodiment, the pharmacological agents that would, in combination with the compounds of the present invention, be most effective in treating or ameliorating one or more symptoms of neurodegenerative disorders include, but are not limited to, Parcopa, Mirapex, Requip, Apokyn, Eldepryl, Zelapar, Azilect, Comtan, Tasmar, Cogentin, Sinemet, Neupro, Symmetrel, Selegiline, Rasagilene, Stalevo, Apokyn, Parlodel, and Artane. In one embodiment, the pharmacological agents that would, in combination with the compounds of the present invention, be most effective in treating or ameliorating one or more symptoms of neurodegenerative disorders include, but are not limited to, Zaronitin, Felbatol, Gabitril, Keppra, Lamictal, Lyrica, Neurontin, Dilantin, Topamax, Trileptal, Depakene, Depakote, Zonegran, Valium, Ativan, Klonopin, Fycompa, and Oxtellar XR. In one embodiment, the pharmacological agents that would, in combination with the compounds of the present invention, be most effective in treating or ameliorating one or more symptoms of neurodegenerative disorders include, but are not limited to, Xenazine, Haldol, Clozaril, Klonopin, Valium, Lexapro, Prozac, Sarafem, Zoloft, Lithobid, Depakene, Depakote, and Lamietal. In one embodiment, the pharmacological agents that would, in combination with the compounds of the present invention, be most effective in treating or ameliorating one or more symptoms of neurodegenerative disorders include, but are not limited to, Aricept, Reminyl, Exelon, Namenda, Risperdal, Zyprexa, and selective serotonin reuptake inhibitors (SSRIs). In one embodiment, the SSRIs are selected from the group consisting of Zimelidine, Celexa (citalopram), Lexapro, Luvox, Paxil (paroxetine), Prozac (fluoxetine), and Zoloft (sertraline).

III. Dosage

Therapeutically effective amount of the compound of formula (1), (1a), or (1b) and/or pharmaceutically acceptable salts thereof will be dependent on the molecule utilized, the subject being treated, the severity and type of the affliction, and the manner and route of administration. For example, a therapeutically effective amount of the compound of Formula (1), (1a), or (1b) and/or pharmaceutically acceptable salts thereof may vary from about 0.001 mg/Kg to about 2000 mg/Kg body weight. In one embodiment, a therapeutically effective amount of the compound of Formula (1), (1a), or (1b) and/or pharmaceutically acceptable salts thereof may vary from about 0.01 mg/Kg to about 1 mg/Kg body weight. In one embodiment, a therapeutically effective amount of the compound of Formula (1), (1a), or (1b) and/or pharmaceutically acceptable salts thereof may vary from about 0.001 mg/Kg to about 0.9 mg/Kg body weight, about 0.8 mg/Kg body weight, about 0.001 mg/Kg to 0.7 mg/Kg body weight, about 0.00.1 mg/Kg to 0.6 mg/Kg body weight about 0.001 mg/Kg to 0.5 mg/Kg body weight about 0.001 mg/Kg to 0.4 mg/Kg body weight, about 0.001 mg/Kg to 0.3 mg/Kg body weight, about 0.001 mg/Kg to 0.2 mg/Kg body weight, about 0.001 mg/Kg to 0.1 mg/Kg body weight, about 0.001 mg/Kg to 0.00 mg/Kg body weight, about 0.001 mg/Kg to 0.08 mg/Kg body weight, about 0.001 mg/Kg to 0.07 mg/Kg body weight, about 0.001 mg/Kg to 0.06 mg/Kg body weight, about 0.001 mg/Kg to 0.05 mg/Kg body weight, about 0.001 mg/Kg to 0.04 mg/Kg body weight, about 0.001 mg/Kg to 0.03 mg/Kg body weight, about 0.001 mg/Kg to 0.02 mg/Kg body weight. 0.01 mg/Kg body weight, about 0.001 mg/Kg to 0.009 mg/Kg body weight, about 0.001 mg/Kg to 0.008 mg/Kg body weight about 0,001 mg/Kg to 0.007 mg/Kg body, about 0.001 mg/Kg to 0.006 mg/Kg body, about 0.001 mg/Kg to 0.005 mg/Kg body weight, about 0.001 mg/Kg to 0.004 mg/Kg body weight, about 0.001 mg/Kg to 0.003 mg/Kg body weight, and about 0.001 mg/Kg to about 0.002 mg/Kg body weight. In one embodiment, a therapeutically effective amount of the compound of Formula (1), (1a), or (1b) and/or pharmaceutical acceptable salts thereof may vary from about 0.001 mg/Kg to about 20 mg/Kg body weight. In one embodiment, a therapeutically effective amount of the compound of Formula (1), (1a), or (1b) and/or pharmaceutically acceptable salts thereof may vary from about 0.001 mg/Kg to about 10 mg/Kg body weight. In one embodiment, a therapeutically effective amount of the compound of Formula (1), (1a), or (1b) and/or pharmaceutically acceptable salts thereof may vary from about 0.001 mg/Kg to about 5 mg/Kg body weight. In one embodiment, a therapeutically effective amount of the compound of Formula (1), (1a), or (1b) and/or pharmaceutically acceptable salts thereof may vary from about 0.001 mg/Kg to about 3 mg/Kg body weight. In one embodiment, a therapeutically effective amount of the compound of Formula (1), (1a), or (1b) and/or pharmaceutically acceptable salts thereof may vary from 0.001 mg/Kg to about 2 mg/Kg body weight. In one embodiment, a therapeutically effective amount of the compound of Formula (1), (1a), or (1b) and/or pharmaceutically acceptable salts thereof may vary from about 0.001 mg/Kg to about 30 mg/Kg body weight. In one embodiment, a therapeutically effective amount of the compound of Formula (1), (1a), or (1b) and/or pharmaceutically acceptable salts thereof may vary from about 0.001 mg/Kg to about 40 mg/Kg body weight. In one embodiment, a therapeutically effective amount of the compound of Formula (1), (1a), or (1b) and/or pharmaceutically acceptable salts thereof may vary from about 0.001 mg/Kg to about 50 mg/Kg body weight. In one embodiment, a therapeutically effective amount of the compound of Formula (1), (1a), or (1b) and/or pharmaceutically acceptable salts thereof may vary in a range selected from the group consisting of about 0.001 mg/kg body weight, about 0.002 mg/kg body weight, about 0.003 mg/kg body weight, about 0.004 mg/kg body weight, about 0.005 mg/kg body weight, about 0.006, mg/kg body weight, about 0.007 mg/kg body weight, about 0.008 mg/kg body weight, about 0.009 mg/kg body weight, about 0.010 mg/kg body weight, about 0.011 mg/kg body weight, about 0.012 mg/kg body weight, about 0.013 mg/kg body weight, about 0.014 mg/kg body weight, about 0.015 mg/kg body weight, about 0.016 mg/kg body weight, about 0.017 mg/kg body weight, about 0.018 mg/kg body weight, about 0.019 mg/kg body weight, about 0.20 mg/kg body weight, about 0.030 mg/kg body weight, about 0.040 mg/kg body weight, about 0.050 mg/kg body weight, about 0.060 mg/kg body weight, about 0.070 mg/kg body weight, about 0.080 mg/kg body weight, about 0.090 mg/kg body weight, about 0.010 mg/kg body weight, about 0.02 mg/kg body weight, about 0.03 mg/kg body weight, about 0.04 mg/kg body weight, about 0.05 mg/kg body weight, about 0.06 mg/kg body weight, about 0.07 mg/kg body weight, about 0.08 mg/kg body weight, about 0.09 mg/kg body weight, about 0.10 mg/kg body weight, about 0.2 mg/kg body weight, about 0.3 mg/kg body weight, about 04. mg/kg body weight, about 0.5 mg/kg body weight, about 0.6 mg/kg body weight, about 0.7 mg/kg body weight, about 0.8 mg/kg body weight, about 0.9 mg/kg body weight, about 1 mg/kg body weight, about 2 mg/kg body weight, about 3 mg/kg body weight, about 4 mg/kg body weight, about 5 mg/kg body weight, about 6 mg/kg body weight, about 7 mg/kg body weight, about 8 mg/kg body weight, about 9 mg/kg body weight, about 10 mg/kg body weight, about 11 mg/kg body weight, about 12 mg/kg body weight, about 13 mg/kg body weight, about 14 mg/kg body weight, about 15 mg/kg body weight, about 16 mg/kg body weight, about 17 mg/kg body weight, about 18 mg/kg body weight, about 19 mg/kg body weight, about 20 mg/kg body weight, about 21 mg/kg body weight, 22 mg/kg body weight, 23 mg/kg body weight, 24 mg/kg body weight, 25 mg/Kg body weight, about 50 mg/Kg body weight, about 75 mg/Kg body weight, about 100 mg/Kg body weight, about 125 mg/Kg body weight, about 150 mg/Kg body weight, about 175 mg/Kg body weight, about 200 mg/Kg body weight, about 225 mg/Kg body weight, about 250 mg/Kg body weight, about 275 mg/Kg body weight about 300 mg/Kg body weight, about 325 mg/Kg body weight, about 350 mg/Kg body weight, about 375 mg/Kg body weight, about 400 mg/Kg body weight, about 425 mg/Kg body weight, about 450 mg/Kg body weight, about 475 mg/Kg body weight, about 500 mg/Kg body weight, about 525 mg/Kg body weight, about 550 mg/Kg body weight, about 575 mg/Kg body weight, about 600 mg/Kg body weight, about 625 mg/Kg body weight, about 650 mg/Kg body weight, about 675 mg/kg body weight, about 700 mg/Kg body weight, about 125 mg/Kg body weight, about mg/Kg body weight, about 775 mg/Kg body weight, about 800 mg/Kg body weight, about 825 mg/Kg body weight, about 850 mg/Kg body weight, about 875 mg/Kg body weight, about 900 mg/Kg body weight, about 925 mg/Kg body weight, about 950 mg/Kg body weight, about 975 mg/Kg body weight, and about 1000 mg/Kg body weight.

In some embodiments, a therapeutically effective amount of the compound of Formula (1), (1a), or (1b) and/or pharmaceutically acceptable salts thereof may vary in a range selected from the group consisting of from about 0.1 mg/kg body weight to about 20 mg/Kg, about 0.2 mg/kg body weight to about 20 mg/Kg, about 0.3 mg/kg body weight to about 20 mg/Kg, about 0.4 mg/kg body weight to about 20 mg/Kg, about 0.5 mg/kg body weight to about 20 mg/Kg, about 0.6 mg/kg body weight to about 20 mg/Kg, about 0.7 mg/kg body weight to about 20 mg/Kg, about 0.8 mg/kg body weight to about 20 mg/Kg, about 0.9 mg/kg body weight to about 20 mg/Kg, about 1.2 mg/kg body weight to about 20 mg/Kg, about 1.1 mg/kg body weight to about 20 mg/Kg, about 1.2 mg/kg body weight to about 20 mg/Kg, about 1.3 mg/kg body weight, to about 20 mg/Kg, about 1.4 mg/kg body weight to about 20 mg/Kg, about 1.5 mg/kg body weight to about 20 mg/Kg, about 1.6 mg/kg body weight to about 20 mg/Kg, about 1.7 mg/kg body weight to about 20 mg/Kg, about 1.8 mg/kg body weight to about 20 mg/Kg, about 1.9 mg/kg body weight to about 20 mg/Kg, about 2 mg/kg body weight to about 20 mg/Kg, about 2/1 mg/kg body weight to about 20 mg/Kg, about 2.2 mg/kg body weight to about 20 mg/Kg, about 2.3 mg/kg body weight to about 20 mg/Kg, about 2.4 mg/kg body weight to about 20 mg/Kg, about 2.5 mg/kg body weight to about 20 mg/Kg, about 2.6 mg/kg body weight to about 20 mg/Kg, about 2.7 mg/kg body weight to about 20 mg/Kg, about 2.8 mg/kg body weight to about 20 mg/Kg, about 2.0 mg/kg body weight to about 20 mg/Kg, about 3 mg/kg body weight to about 20 mg/Kg, about 3.1 mg/kg body weight to about 20 mg/Kg, about 3.2 mg/kg body weight to about 20 mg/Kg, about 3.3 mg/kg body weight to about 20 mg/Kg, about 3.4 mg/kg body weight to about 20 mg/Kg, about 3.5 mg/kg body weight to about 20 mg/Kg, about 3.6 mg/kg body weight to about 20 mg/Kg, about 3.7 mg/kg body weight to about 20 mg/Kg, about 3.8 mg/kg body weight to about 20 mg/Kg, about 3.9 mg/kg body weight to about 20 mg/Kg, about 4 mg/kg body weight to about 20 mg/Kg, about 4.1 mg/kg body weight to about 20 mg/Kg, about 4.2 mg/kg body weight to about 20 mg/Kg, about 4.3 mg/kg body weight to about 20 mg/Kg, about 4.4 mg/kg body weight to about 20 mg/Kg, about 15 mg/kg body weight to about 20 mg/Kg, about 4.6 mg/kg body weight to about 20 mg/Kg, about 4.7 mg/kg body weight to about 2.0 mg/Kg, about 4.8 mg/kg body weight to about 20 mg/Kg, about 4.9 mg/kg body weight to about 20 mg/Kg, about 5 mg/kg body weight to about 20 mg/Kg, about 5.1 mg/kg body weight to about 20 mg/Kg, about 5.2 mg/kg body weight to about 20 mg/Kg, about 5.3 mg/kg body weight to about 20 mg/Kg, about 5.4 mg/kg body weight to about 20 mg/Kg, about 5.5 mg/kg body weight to about 20 mg/Kg, about 5.6 mg/kg body weight to about 20 mg/Kg, about 5.7 mg/kg body weight to about 20 mg/Kg, about 5.8 mg/kg body weight to about 20 mg/Kg, about 5.9 mg/kg body weight to about 20 mg/Kg, about 6 mg/kg body weight to about 20 mg/Kg, about 6.1 mg/kg body weight to about 20 mg/Kg, about 6.2 mg/kg body weight to about 20 mg/Kg, about 0.3 mg/kg body weight to about 20 mg/Kg, about 6.4 mg/kg body weight to about 20 mg/Kg, about 6.5 mg/kg body weight to about 20 mg/Kg, about 6.0 mg/kg body weight to about 20 mg/Kg, about 6.7 mg/kg body weight to about 20 mg/Kg, about 6.8 mg/kg body weight to about 20 mg/Kg, about 6.9 mg/kg body weight to about 20 mg/Kg, about 7 mg/kg body weight to about 20 mg/Kg, about 7.1 mg/kg body weight, to about 20 mg/Kg, about 7.2 mg/kg body weight to about 20 mg/Kg, about 7.3 mg/kg body weight to about 20 mg/Kg, about 7.4 mg/kg body weight to about 20 mg/Kg, about 7.5 mg/kg body weight to about 20 mg/Kg, about 7.6 mg/kg body weight, to about 20 mg/Kg, about 7.7 mg/kg, body weight to about 20 mg/Kg, about 7.8 mg/kg body weight to about 20 mg/Kg, about 7.9 mg/kg body weight to about 20 mg/Kg, about 8 mg/kg body weight to about 20 mg/Kg, about 8.1 mg/kg body weight to about 20 mg/Kg, about 8.2 mg/kg body weight to about 20 mg/Kg, about 8.3 mg/kg body weight to about 20 mg/Kg, about 8.4 mg/kg body weight to about 20 mg/Kg, about 8.5 mg/kg body weight, to about 20 mg/Kg, about 8.6 mg/kg body weight to about 20 mg/Kg, about 8.7 mg/kg body weight to about 20 mg/Kg, about 8.8 mg/kg body weight to about 20 mg/Kg, about 8.9 mg/kg body weight to about 20 mg/Kg, about 9 mg/kg body weight to about 20 mg/Kg, about 9.1 mg/kg body weight to about 20 mg/Kg, about 9.2 mg/Kg body weight to about 20 mg/Kg, about 9.3 mg/kg body weight to about 20 mg/Kg, about 9.4 mg/kg body weight to about 20 mg/Kg, about 9.5 mg/kg body weight to about 20 mg/Kg, about 9.6 mg/kg body weight to about 20 mg/Kg, about 9.7 mg/kg body weight to about 20 mg/Kg, about 9.8 mg/kg body weight to about 20 mg/Kg, about 9.9 mg/kg body weight to about 20 mg/Kg, about 10 mg/kg body weight to about 20 mg/Kg, about 10.1 mg/kg body weight to about 20 mg/Kg, about 10.2 mg/kg body weight to about 20 mg/Kg, about 10.3 mg/kg body weight to about 20 mg/Kg, about 10.4 mg/kg body weight to about 20 mg/Kg, about 10.5 mg/kg body weight to about 20 mg/Kg, about 10.6 mg/kg body weight to about 20 mg/Kg, about 10.7 mg/kg body weight to about 20 mg/Kg, about 10.8 mg/kg body weight to about 20 mg/Kg, about 10.9 mg/kg body weight to about 20 mg/Kg, about 11 mg/kg body weight to about 20 mg/Kg, about 11.1 mg/kg body weight to about 20 mg/Kg, about 11.2 mg/kg body weight to about 20 mg/Kg, about 11.3 mg/kg body weight to about 20 mg/Kg, about 11.4 mg/kg body weight to about 20 mg/Kg, about 11.5 mg/kg body weight to about 20 mg/Kg, about 11.6 mg/kg body weight to about 20 mg/Kg, about 11.7 mg/kg body weight to about 20 mg/Kg, about 11.8 mg/kg body weight to about 20 mg/Kg, about 11.9 mg/kg body weight to about 20 mg/Kg, about 12 mg/kg body weight to about 20 mg/Kg, about 12.1 mg/kg body weight to about 20 mg/Kg, about 12.2 mg/kg body weight 10 about 20 mg/Kg, about 12.3 mg/kg body weight to about 20 mg/Kg, about 12.4 mg/kg body weight to about 20 mg/Kg, about 12.5 mg/kg body weight to about 20 mg/Kg, about 12.6 mg/kg body weight to about 20 mg/Kg, about 12.7 mg/kg body weight to about 20 mg/Kg, about 12.8 mg/kg body weight to about 20 mg/Kg, about 12.9 mg/kg body weight to about 20 mg/Kg, about 13 mg/kg body weight to about 20 mg/Kg, about 13.1 mg/kg body weight to about 20 mg/Kg, about 13.2 mg/kg body weight to about 20 mg/Kg, about 13.3 mg/kg body weight to about 20 mg/Kg, about 13.4 mg/kg body weight to about 20 mg/Kg, about 13.5 mg/kg body weight to about 20 mg/Kg, about 13.6 mg/kg body weight to about 20 mg/Kg, about 13.7 mg/kg body weight to about 20 mg/Kg, about 13.8 mg/kg body weight to about 20 mg/Kg, about 13.9 mg/kg. body weight to about 20 mg/Kg, about 14 mg/kg body weight to about 20 mg/Kg, about 14.1 mg/kg body weight to about 20 mg/Kg, about 14.2 mg/kg body weight to about 20 mg/Kg, about 14.3 mg/kg body weight to about 20 mg/Kg, about 14.4 mg/kg body weight to about 20 mg/Kg, about 14.5 mg/kg body weight to about 20 mg/Kg, about 14.6 mg/kg body weight to about 20 mg/Kg, about 14.7 mg/kg body weight to about 20 mg/Kg, about 14.8 mg/kg body weight to about 20 mg/Kg, about 14.9 mg/kg body weight to about 20 mg/Kg, about 15 mg/kg body weight to about 20 mg/Kg, about 15.1 mg/kg body weight to about 20 mg/Kg, about 15.2 mg/kg body weight to about 20 mg/Kg, about 15.3 mg/kg body weight to about 20 mg/Kg, about 15.4 mg/kg body weight to about 20 mg/Kg, about 15.5 mg/kg body weight to about 20 mg/Kg, about 15.6 mg/kg body weight to about 20 mg/Kg, about 15.7 mg/kg body weight to about 20 mg/Kg, about 15.8 mg/kg body weight to about 20 mg/Kg, about 15.9 mg/kg body weight to about 20 mg/Kg, about 16 mg/kg body weight to about 20 mg/Kg, about 16.1 mg/kg body weight to about 20 mg/Kg, about 16.2 mg/kg body weight to about 20 mg/Kg, about 16.3 mg/kg body weight to about 20 mg/Kg, about 16.4 mg/kg body weight to about 20 mg/Kg, about 16.5 mg/kg body weight to about 20 mg/Kg, about 16.6 mg/kg body weight to about 20 mg/Kg, about 16.7 mg/kg body weight to about 20 mg/Kg, about 16.8 mg/kg body weight to about 20 mg/Kg, about 16.9 mg/kg body weight to about 20 mg/Kg, about 17 mg/kg body weight to about 20 mg/Kg, about 17.1 mg/kg body weight to about 20 mg/Kg, about 17.2 mg/kg body weight to about 20 mg/Kg, about 17.3 mg/kg body weight to about 20 mg/Kg, about 17.4 mg/kg body weight to about 20 mg/kg, about 17.5 mg/kg body weight to about 20 mg/Kg, about 17.6 mg/kg body weight to about 20 mg/Kg, about 17.7 mg/kg body weight to about 20 mg/Kg, about 17.8 mg/kg body weight to about 20 mg/Kg, about 17.9 mg/kg body weight to about 20 mg/Kg, about 18 mg/kg body weight to about 20 mg/Kg, about 18.1 mg/kg body weight to about 20 mg/Kg, about 18.2 mg/kg body weight to about 20 mg/Kg, about 18.3 mg/kg body weight to about 20 mg/Kg, about 18.4 mg/kg body weight to about 20 mg/Kg, about 18.5 mg/kg body weight to about 20 mg/Kg, about 18.6 mg/kg body weight to about 20 mg/Kg, about 18.7 mg/kg body weight to about 20 mg/Kg, about 18.8 mg/kg body weight to about 20 mg/Kg, about 18.9 mg/kg body weight to about 20 mg/Kg, about 19 mg/kg body weight to about 20 mg/Kg, about 19.1 mg/kg body weight to about 20 mg/Kg, about 19.2 mg/kg body weight to about 20 mg/Kg, about 19.3 mg/kg body weight to about 20 mg/Kg, about 19.4 mg/kg body weight to about 20 mg/Kg, about 19.5 mg/kg body weight to about 20 mg/Kg, about 19.6 mg/kg body weight to about 20 mg/Kg, about 19.7 mg/kg body weight to about 20 mg/Kg, about 19.8 mg/kg body weight to about 20 mg/Kg, and about 19.9 mg/kg body weight to about 20 mg/Kg.

In some embodiments, a therapeutically effective amount of the compound of Formula (1), (1a), or (1b) and/or pharmaceutically acceptable salts thereof is equal to or less than 160 mg/m$^2$ but greater than 0 mg/m$^2$. In some embodiments, a therapeutically effective amount of the compound of Formula (1), (1a), or (1b) and/or pharmaceutically acceptable sales thereof is selected from the group consisting of less than about 160 mg/m$^2$ but greater than about 0.001 mg/m$^2$, less than about 155 mg/m$^2$ but greater than about 0.001 mg/m$^2$, less than about 150 mg/m$^2$ but greater than about 0.001 mg/m$^2$, less than about 145 mg/m$^2$ but greater than about 0.001 mg/m$^2$, less than about 140 mg/m$^2$ but greater than about 0.001 mg/m$^2$, less than about 135 mg/m$^2$ but greater than about 0.001 mg/m$^2$, less than about 130 mg/m$^2$ but greater than about 0.001 mg/m$^2$, less than about 125 mg/m$^2$ but greater than about 0.001 mg/m$^2$, less than about 120 mg/m$^2$ but greater than about 0.001 mg/m$^2$, less than about 115 mg/m$^2$ but greater than about 0.001 mg/m$^2$, less than about 110 mg/m$^2$ but greater than about 0.001 mg/m$^2$, less than about 105 mg/m$^2$ but greater than about 0.001 mg/m$^2$, less than about 100 mg/m$^2$ but greater than about 0.001 mg/m$^2$, less than about 95 mg/m$^2$ but greater than about 0.001 mg/m$^2$, less than about 90 mg/m$^2$ but greater than about 0.001 mg/m$^2$, less than about 85 mg/m$^2$ but greater than about 0.001 mg/m$^2$, less than about 80 mg/m$^2$ but greater than about 0.001 mg/m$^2$, less than about 75 mg/m$^2$ but greater than about 0.001 mg/m$^2$, less than about 70 mg/m$^2$ but greater than about 0.001 mg/m$^2$, less than about 65 mg/m$^2$ but greater than about 0.001 mg/m$^2$, less than about 60 mg/m$^2$ but greater than about 0.001 mg/m$^2$, less than about 55 mg/m$^2$ but greater than about 0.001 mg/m$^2$, less than about 50 mg/m$^2$ but greater than about 0.001 mg/m$^2$, less than about 45 mg/m$^2$ but greater than about 0.001 mg/m$^2$, less than about 40 mg/m$^2$ but greater than about 0.001 mg/m$^2$, less than about 35 mg/m$^2$ but greater than about 0.001 mg/m$^2$, less than about 30 mg/m$^2$ but greater than about 0.001 mg/m$^2$, less than about 25 mg/m$^2$ but greater than about 0.001 mg/m$^2$, less than about 20 mg/m$^2$ but greater than about: 0.00! mg/m$^2$, less than about 15 mg/m$^2$ but greater than about 0.001 mg/m$^2$, less than about 10 mg/m$^2$ but greater than about 0.001 mg/m$^2$, and leas than about 5 mg/m$^2$ but greater than about 0.001 mg/m$^2$.

In some embodiments, a therapeutically effective amount of the compound of Formula (1), (1a), or (1b) and/or pharmaceutically acceptable salts thereof is selected from the group consisting of from about 0.001 mg/m$^2$ to about 160 mg/m$^2$, from about 0.001 mg/m$^2$ to about 155 mg/m$^2$, from about 0.001 mg/m$^2$ to about 150 mg/m$^2$, from about 0.001 mg/m$^2$ to about 145 mg/m$^2$, from about 0.001 mg/m$^2$ to about 140 mg/m$^2$, from about 0.001 mg/m$^2$ to about 135 mg/m$^2$, from about 0.001 mg/m$^2$ to about 130 mg/m$^2$, from about 0.001 mg/m$^2$ to about 125 mg/m$^2$, from about 0.001 mg/m$^2$ to about 120 mg/m$^2$, from about 0.001 mg/m$^2$ to about 115 mg/m$^2$, from about 0.001 mg/m$^2$ to about 110 mg/m$^2$, from about 0.001 mg/m$^2$ to about 105 mg/m$^2$, from about 0.001 mg/m$^2$ to about 100 mg/m$^2$, from about 0.001 mg/m$^2$ to about 95 mg/m$^2$, from about 0.001 mg/m$^2$ to about 90 mg/m$^2$, from about 0.001 mg/m$^2$ to about 85 mg/m$^2$, from about 0.001 mg/m$^2$ to about 80 mg/m$^2$, from about 0.001 mg/m$^2$ to about 75 mg/m$^2$, from about 0.001 mg/m$^2$ to about 70 mg/m$^2$, from about 0.001 mg/m$^2$ to about 65 mg/m$^2$, from about 0.001 mg/m$^2$ to about 60 mg/m$^2$, from about 0.001 mg/m$^2$ to about 55 mg/m$^2$, from about 0.001 mg/m$^2$ to about 50 mg/m$^2$, from about 0.001 mg/m$^2$ to about 45 mg/m$^2$, from about 0.001 mg/m$^2$ to about 40 mg/m$^2$, from about 0.001 mg/m$^2$ to about 35 mg/m$^2$, from about 0.001 mg/m$^2$ to about 30 mg/m$^2$, from about 0.001 mg/m$^2$ to about 25 mg/m$^2$, from about 0.001 mg/m$^2$ to about 20 mg/m$^2$, from about 0.001 mg/m$^2$ to about 15 mg/m$^2$, from about 0.001 mg/m$^2$ to about 10 mg/m$^2$, from about 0.001 mg/m$^2$ to about 5 mg/m$^2$, from about 0.1 mg/m$^2$ to about 10 mg/m$^2$, from about 0.1 mg/m$^2$ to about 9 mg/m$^2$, from about 0.1 mg/m$^2$ to about 8 mg/m$^2$, from about 0.1 mg/m$^2$ to about 7 mg/m$^2$, from about 0.1 mg/m$^2$ to about 6 mg/m$^2$ from about 0.1 mg/m$^2$ to about 5 mg/m$^2$, from about 0.1 mg/m$^2$ to about 4 mg/m$^2$, from about 0.1 mg/m$^2$ to about 3 mg/m$^2$, from about 0.1 mg/m$^2$ to about 2 mg/m$^2$, and from about 0.1 mg/m$^2$ to about 1 mg/m$^2$.

In some embodiments, a therapeutically effective amount of the compound of Formula (1), (1a), or (1b) and/or pharmaceutically acceptable salts thereof is selected from the group consisting of about 0.01 mg/m$^2$, about 0.02 mg/m$^2$, about 0.03 mg/m$^2$, about 0.04 mg/m$^2$, about 0.05 mg/m$^2$, about 0.06 mg/m$^2$, about 0.07 mg/m$^2$, about 0.08 mg/m$^2$, about 0.09 mg/m$^2$, and about 0.1 mg/m$^2$.

In some embodiments, a therapeutically effective amount of the compound of Formula (1), (1a), or (1b) and/or pharmaceutically acceptable salts thereof is selected from the group consisting of about 0.1 mg/m$^2$, about 0.2 mg/m$^2$, about 0.3 mg/m$^2$, about 0.4 mg/m$^2$, about 0.5 mg/m$^2$, about 0.6 mg/m$^2$, about 0.7 mg/m$^2$, about 0.8 mg/m$^2$, about 0.9 mg/m$^2$, about 1 mg/m$^2$, about 1.1 mg/m$^2$, about 1.2 mg/m$^2$, about 1.3 mg/m$^2$, about 1.4 mg/m$^2$, about 1.5 mg/m$^2$, about 1.6 mg/m$^2$, about 1.7 mg/m$^2$, about 1.8 mg/m$^2$, about 1.9 mg/m$^2$, about 2 mg/m$^2$, about 2.1 mg/m$^2$, about 2.2 mg/m$^2$, about 2.3 mg/m$^2$, about 2.4 mg/m$^2$, about 2.5 mg/m$^2$, about 2.6 mg/m$^2$, about 2.7 mg/m$^2$, about 2.8 mg/m$^2$, about 2.9 gm/m$^2$, and about 3 mg/m$^2$.

In some embodiments, a therapeutically effective amount of the compound of Formula (1), (1a), or (1b) and/or pharmaceutically acceptable salts thereof is selected from the group consisting of about 4 mg/m$^2$, about 5 mg/m$^2$, about 6 mg/m$^2$, about 7 mg/m$^2$, about 8 mg/m$^2$, about 9 mg/m$^2$, about 10 mg/m$^2$, about 11 mg/m$^2$, about 12 mg/m$^2$, about 13 mg/m$^2$, about 14 mg/m$^2$, about 15 mg/m$^2$, about 16 mg/m$^2$, about 17 mg/m$^2$, about 18 mg/m$^2$, about 19 mg/m$^2$, about 20 mg/m$^2$, about 21 mg/m$^2$, about 22 mg/m$^2$, about 23 gm/m$^2$, about 24 mg/m$^2$, and about 25 mg/m$^2$.

In some embodiments, a therapeutically effective amount of the compound of Formula (1), (1a), or (1b) and/or pharmaceutically acceptable salts thereof is selected from the group consisting of about 4.1 mg/m$^2$, about 4.2 mg/m$^2$, about 4.3 mg/m$^2$, about 4.4 mg/m$^2$, about 4.5 mg/m$^2$, about 4.6 mg/m$^2$, about 4.7 mg/m$^2$, about 4.8 mg/m$^2$, about 4.9 gm/m$^2$, about 5 mg/m$^2$, about 5.1 mg/m$^2$, about 5.2 mg/m$^2$, about 5.3 mg/m$^2$, about 5.4 mg/m$^2$, about 5.5 mg/m$^2$, about 5.6 mg/m$^2$, about 5.7 mg/m$^2$, about 5.8 mg/m$^2$, about 5.9 mg/m$^2$, about 6 mg/m$^2$, about 6.1 mg/m$^2$, about 6.2 mg/m$^2$, about 6.3 mg/m$^2$, about 6.4 mg/m$^2$, about 6.5 mg/m$^2$, about 6.6 mg/m², about 6.7 mg/m², about 6.8 mg/m², about 6.9 mg/m², about 7 mg/m², about 7.1 mg/m², about 7.2 mg/m², about 7.3 mg/m², about 7.4 mg/m², about 7.5 mg/m², about 7.6 mg/m², about 7.7 mg/m², about 7.8 mg/m², about 7.9 mg/m², and about 8 mg/m².

In some embodiments, a therapeutically effective amount of the compound of Formula (1), (1a), or (1b) and/or pharmaceutically acceptable salts thereof is selected from the group consisting of about 20.1 mg/m², about 20.2 mg/m², about 20.3 mg/m², about 20.4 mg/m², about 20.5 mg/m², about 20.6 mg/m², about 20.7 mg/m², about 20.8 mg/m², about 20.9 mg/m², about 21 mg/m², about 21.1 mg/m², about 21.2 mg/m², about 21.3 mg/m², about 21.4 mg/m², about 21.5 mg/m², about 21.6 mg/m², about 21.7 mg/m², about 21.8 mg/m², about 21.9 mg/m², about 22 mg/m², about 22.1 mg/m², about 22.2 mg/m², about 22.3 mg/m², about 22.4 mg/m², about 22.5 mg/m², about 22.6 mg/m², about 22.7 mg/m², about 22.8 mg/m², about 22.9 mg/m², about 23 mg/m², about 23.1 mg/m², about 23.2 mg/m², about 23.3 mg/m², about 23.4 mg/m², about 23.5 mg/m², about 23.6 mg/m², about 23.7 mg/m², about 23.8 mg/m², about 23.9 mg/m², and about 24 mg/m².

In some embodiments, a therapeutically effective amount of the compound of Formula (1), (1a), or (1b) and/or pharmaceutically acceptable salts thereof is selected from the group consisting of about 0.1 mg/m², about 0.2 mg/m², about 0.3 mg/m², about 0.4 mg/m², about 0.5 mg/m², about 0.6 mg/m², about 0.7 mg/m², about 0.8 mg/m², about 0.9 mg/m², about 1 mg/m², about 1.1 mg/m², about 1.2 mg/m², about 1.3 mg/m², about 1.4 mg/m², about 1.5 mg/m², about 1.6 mg/m², about 1.7 mg/m², about 1.8 mg/m², about 1.9 mg/m², about 2 mg/m², about 2.1 mg/m², about 2.2 mg/m², about 2.3 mg/m², about 2.4 mg/m², about 2.5 mg/m², about 2.6 mg/m², about 2.7 mg/m², about 2.8 mg/m², about 2.9 mg/m², about 3 mg/m², about 3.1 mg/m², about 3.2 mg/m², about 3.3 mg/m², about 3.4 mg/m², about 3.5 mg/m², about 3.6 mg/m², about 3.7 mg/m², about 3.8 mg/m², about 3.9 mg/m², about 4 mg/m², about 4.1 mg/m², about 4.2 mg/m², about 4.3 mg/m², about 4.4 mg/m², about 4.5 mg/m², about 4.6 mg/m², about 4.7 mg/m², about 4.8 mg/m², about 4.9 mg/m², about 5 mg/m², about 5.1 mg/m², about 5.2 mg/m², about 5.3 mg/m², about 5.4 mg/m², about 5.5 mg/m², about 5.6 mg/m², about 5.7 mg/m², about 5.8 mg/m², about 5.9 mg/m², about 6 mg/m², about 6.1 mg/m², about 6.2 mg/m², about 6.3 mg/m², about 6.4 mg/m², about 6.5 mg/m², about 6.6 mg/m², about 6.7 mg/m², about 6.8 mg/m², about 6.9 mg/m², about 7 mg/m², about 7.1 mg/m², about 7.2 mg/m², about 7.3 mg/m², about 7.4 mg/m², about 7.5 mg/m², about 7.6 mg/m², about 7.7 mg/m², about 7.8 mg/m², about 7.9 mg/m², about 8 mg/m², about 8.6 mg/m², about 8.7 mg/m², about 8.8 mg/m², about 8.9 mg/m², about 9 mg/m², about 9.1 mg/m², about 9.2 mg/m², about 9.3 mg/m², about 9.4 mg/m², about 9.5 mg/m², about 9.6 mg/m², about 9.7 mg/m², about 9.8 mg/m², about 9.9 mg/m², and about 10 mg/m².

III. Methods

In one embodiment, the present invention provides disease-modifying treatments for neurodegenerative disorders. In one embodiment, the method of the present invention delays worsening of symptoms and/or progression of the underlying neurodegenerative disorders. In one embodiment, the present invention provides a method of treating or ameliorating one or more symptoms of a neurodegenerative disorder. In one embodiment, the present invention provides a neuroprotective therapy against neurodegenerative disorders. In one embodiment, the present invention provides neurorestorative interventions against neurodegenerative disorders. In one embodiment, the terms "disease-modifying treatments" or "disease-modifying therapies" as used herein mean treatments or interventions that affect the underlying pathophysiology of the disease and have a beneficial outcome on the course of the disease. In one embodiment, the method comprises administering to a subject in need thereof, a compound having the structure of Formula (1), (1a), or (1b):

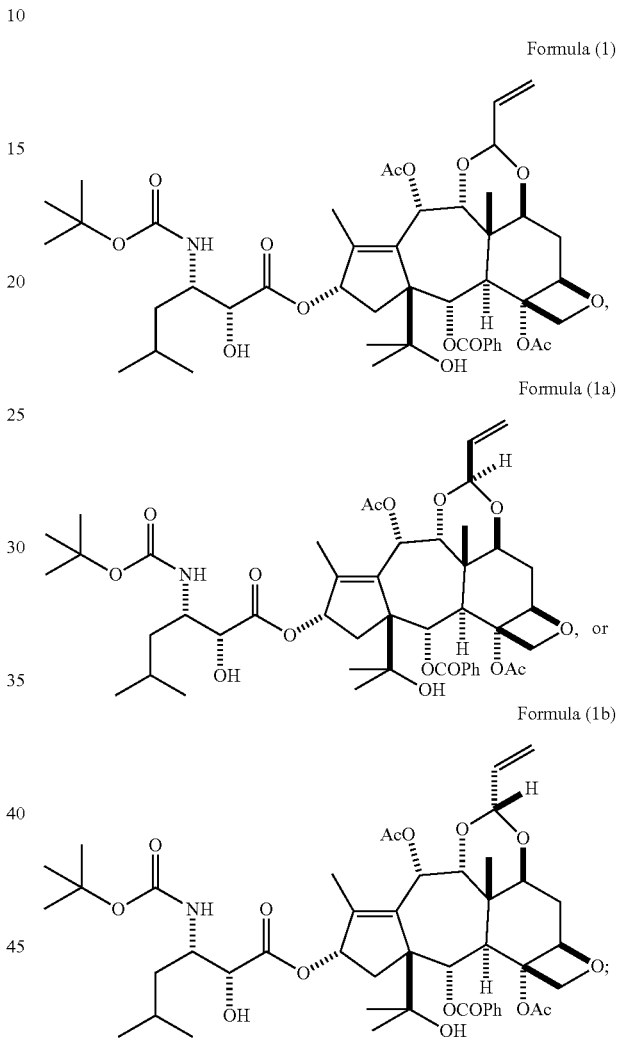

and/or a pharmaceutically acceptable salt thereof. In one embodiment, the compound having the structure of Formula (1), (1a), or (1b) and/or a pharmaceutically acceptable salt neuroprotective effect. In some embodiments, the present invention provides a method of treating or preventing progression of a neurodegenerative disorder in a subject at risk for developing a tauopathy, comprising (a) screening for the subject for the presence of tau protein in the brain; and (b) administering to the subject in need thereof, a compound having the structure of Formula (1), (1a) or (1b) and/or a pharmaceutically acceptable salt thereof if presence of tau protein in the brain is established. In one embodiment, the a tauopathy selected from the group consisting of Alzheimer's disease (AD), frontotemproal dementia with Parkinsonism linked to chromosome 17 (FTDP-17), progressive supranuclear palsy (PSP), Pick's disease, corticobasal degeneration and multiple system atrophy (MSA). In one embodiment, the compound having the structure of Formula (1), (1a), or (1b) and/or a pharmaceutically acceptable salt thereof is administered to the subject at a dose ranging from about 0.001 mg/Kg to about 2000 mg/Kg body weight or from about 0.001 mg/m² to about 160 mg/m². In some embodiments, the compound having the structure of Formula (1) and/or a pharmaceutically acceptable salt thereof is administered to the subject at a dose that is equal to or less than 160 mg/m² but greater than 0 mg/m². In one embodiment, the compound of Formula (1), (1a), or (1b) and/or the pharmaceutically acceptable salt thereof is administered to the subject in need in a single dose or in divided doses. In one embodiment, the compound of Formula (1), (1a), or (1b) and/or the pharmaceutically acceptable salt thereof is administered to the subject in need in a single dose per day or in divided doses per day. In one embodiment, wherein the compound of Formula (1), (1a), or (1b) and/or a pharmaceutically acceptable salt thereof dose is administered in two or more equally divided doses per day. In one embodiment, wherein the compound of Formula (1), (1a), or (1b) and/or the pharmaceutically acceptable salt thereof is administered in two and/or more unequally divided doses per day. In one embodiment, the compound of Formula (1), (1a), or (1b) and/or the pharmaceutically acceptable salt thereof is administered to the subject in need in two and/or three divided doses per day. In one embodiment, wherein the compound of Formula (1), (1a), or (1b) and/or the pharmaceutically acceptable salt thereof dose is administered in two and/or four divided doses per day. In one embodiment, the compound of Formula (1), (1a), or (1b) and/or the pharmaceutically acceptable salts thereof administered to the subject in need at least once daily for at least two successive days. In one embodiment, the compound of Formula (1), (1a), or (1b) and/or the pharmaceutically acceptable salt thereof is administered to the subject in need at least once daily on alternative days. In one embodiment, the compound of Formula (1), (1a), or (1b) and/or the pharmaceutically acceptable salt thereof is administered to the subject in need weekly. In one embodiment, the compound of Formula (1), (1a), or (1b) and/or the pbarmaceutically acceptable salt thereof is administered to the subject in need weekly divided into equal and/or unequal doses. In one embodiment, the compound of Formula (1), (1a), or (1b) and/or the pharmaceutically acceptable salt thereof is administered to the subject in need weekly given either on three alternate days and/or 6 times per week. In one embodiment, the compound of Formula (1), (1a), or (1b) and/or the pharmaceutically acceptable salt thereof is administered to the subject in need in divided doses on alternate days, every third day, every fourth day, every fifth day, every sixth day and/or weekly. In one embodiment, the compound of Formula (1), (1a), or (1b) and/or the pharmaceutically acceptable salt there of is administered to the subject in need monthly. In one embodiment, the compound of Formula (1), (1a), or (1b) and/or the pharmaceutically acceptable salt thereof is administered to the subject in need in a single dose per month and/or in divided doses per month. In one embodiment, wherein the compound of Formula (1), (1a), or (1b) and/or a pharmaceutically acceptable salt thereof dose is administered in two and/or more equally divided doses per month. In one embodiment, wherein the compound of Formula (1), (1a), or (1b) and/or the pharmaceutically acceptable salt thereof dose is administered in two and/or more unequally divided doses per month. In one embodiment, the compound of Formula (1), (1a), or (1b) and/or the pharmaceutically acceptable salt thereof is administered to the subject in need in two and/or three divided doses per month. In one embodiment, wherein the compound of Formula (1), (1a), or (1b) and/or the pharmaceutically acceptable salt thereof dose is administered in two and/or four divided doses per month. In one embodiment, the compound of Formula (1), (1a), or (1b) and/or the pharmaceutically acceptable salt thereof is administered to the subject in need at least once monthly for at least two successive months. In one embodiment, the compound of Formula (1), (1a), or (1b) and/or the pharmaceutically acceptable salt thereof is administered to the subject in need at least once monthly on alternative months. In one embodiment, the methods of the present invention provide a dosing regimen comprising directing the compound of Formula (1), (1a), or (1b) and/or the pharmaceutically acceptable salt thereof to be administered to a subject in need thereof in an amount corresponding to a dosing level disclosed herein for up to 1 day, up to 2 days, up to 3 days, up to 4 days, up to 5 days, up to 6 days, up to 7 days, up to 8 days, up to 9 days, up to 10 days, up to 11 days, up to 12 days, up to 13 days, up to 14 days, up to 15 days, up to 29 days, or up to 30 days.

In one embodiment, the methods of the present invention provide a dosing regimen comprising directing the compound of Formula (1), (1a), or (1b) and/or the pharmaceutically acceptable salt thereof to be administered to a subject in need thereof in a dose of about 3 mg/Kg at least every three weeks. In one embodiment, the dosing regimen comprises administering a compound of Formula (1), (1a), or (1b) and/or a pharmaceutically acceptable salt thereof to a subject in need thereof in a dose of about 3.5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 4 mg/Kg at least every three weeks. In one embodiment, the dosing regimen comprises administering a compound of Formula (1), (1a) or (1b) and/or a pharmaceutically acceptable salt thereof to a subject in need thereof in a dose of about 4.5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 3.5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 6 mg/Kg at least every three weeks. In one embodiment, the dosing regimen comprises administering a compound of Formula (1), (1a), or (1b) and/or a pharmaceutically acceptable salt thereof to a subject in need thereof in a dose of about 6.5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 8 mg/Kg at least every three weeks. In one embodiment, the dosing regimen comprises administering a compound of Formula (1), (1a), or (1b) and/or a pharmaceutically acceptable salt thereof to a subject in need thereof in a dose of about 7.5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 9 mg/Kg at least every three weeks. In one embodiment, the dosing regimen comprises administering a compound of Formula (1), (1a), or (1b) and/or a pharmaceutically acceptable salt thereof to a subject in need thereof in a dose of about 8.5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 9 mg/Kg at least every three weeks. In one embodiment, the dosing regimen comprises administering a compound of Formula (1), (1a), or (1b) and/or a pharmaceutically acceptable salt thereof to a subject in need thereof in a dose of about 9.5 mg/Kg at least every three weeks. In one embodiment, the dosing regimen comprises administering a compound of Formula (1), (1a), or (1b) and/or a pharmaceutically acceptable salt thereof to a subject in need thereof in a dose of about 10 mg/Kg at least every three weeks.

In one embodiment, the methods of the present invention provide a dosing regimen comprising directing the compound of Formula (1), (1a), or (1b) and/or the pharmaceutically acceptable salt thereof to be administered to a subject in need thereof in a dose of about 80 mg/Kg every three weeks, about 70 mg/Kg every three weeks, about 60 mg/Kg every three weeks, about 50 mg/Kg every three weeks, about 40 mg/Kg every three weeks, about 30 mg/Kg every three weeks, about 20 mg/Kg every three weeks, about 10 mg/Kg every three weeks, about 80 mg/Kg every three weeks, about 75 mg/Kg every three weeks, about 70 mg/Kg every three weeks, about 65 mg/Kg every three weeks, about 60 mg/Kg every three weeks, about 55 mg/Kg every three weeks, about 50 mg/Kg every three weeks, about 45 mg/Kg every three weeks, about 40 mg/Kg every three weeks, about 35 mg/Kg every three weeks, about 30 mg/Kg every three weeks, about 25 mg/Kg every three weeks, about 20 mg/Kg every three weeks, about 15 mg/Kg every three weeks, about 10 mg/Kg every three weeks, about 5 mg/Kg every three weeks, about 8 mg/Kg every three weeks, about 16 mg/Kg every three weeks, about 32 mg/Kg every three weeks, about 48 mg/Kg every three weeks, about 64 mg/Kg every three weeks, and about 80 mg/Kg every three weeks. In one embodiment, the methods of the present invention provide a dosing regimen comprising directing the compound of Formula (1), (1a), or (1b) and/or the pharmaceutically acceptable salt thereof to be administered to a subject in need thereof in a dose of about 16 mg/Kg every three weeks, about 32 mg/Kg every three weeks, about 64 mg/Kg every three weeks, about 96 mg/Kg every three weeks, about 128 mg/Kg every three weeks, and about 160 mg/Kg every three weeks. In one embodiment, the methods of the present invention provide a dosing regimen comprising directing the compound of Formula (1), (1a), or (1b) and/or the pharmaceutically acceptable salt thereof to be administered to a subject in need thereof in a dose of about 13 mg/Kg every three weeks, about 27 mg/Kg every three weeks, about 53 mg/Kg every three weeks, about 80 mg/Kg every three weeks, about 107 mg/Kg every three weeks, about 133 mg/Kg. In one embodiment, the methods of the present invention provide a dosing regimen comprising directing the compound of Formula (1), (1a), or (1b) and/or the pharmaceutically acceptable salt thereof to be administered to a subject in need thereof in a dose of about 20 mg/Kg every three weeks, about 40 mg/Kg every three weeks, about 80 mg/Kg every three weeks, about 120 mg/Kg every three weeks, about 160 mg/Kg every three weeks, and about 200 mg/Kg every three weeks. In one embodiment, the methods of the present invention provide a dosing regimen comprising directing the compound of Formula (1), (1a), or (1b) and/or the pharmaceutically acceptable salt thereof to be administered to a subject in need thereof in a dose of about 27 mg/Kg every three weeks, about 53 mg/Kg every three weeks, about 107 mg/Kg every three weeks, about 160 mg/Kg every three weeks, about 213 mg/Kg every three weeks, and about 267 mg/Kg every three weeks. In one embodiment, the dosing regimen in accordance with the present invention comprises directing the dosing regimen comprising directing the compound of Formula (1), (1a), or (1b) and/or the pharmaceutically acceptable salt thereof to be administered to a subject in need thereof by a route selected from the group consisting of oral administration, sublingual administration, buccal administration, nasal administration, transdermal administration, vaginal administration, rectal administration, intravenous administration, subcutaneous administration, intraperitoneal administration, parenteral administration, intramuscular administration, depot administration, topical administration, intrauterine administration, inhalation administration, implant administration and ocular administration.

The methods of the present invention are suitable for treating and/or ameliorating symptoms of various neurodegenerative disorders. In one embodiment, the neurodegenerative disorder is selected from the group consisting of Alzheimer's disease (AD), Parkinsonian syndromes (PD), Huntington's disease (HD), Dementia pugilistica (DP), Prion diseases, cerebral amyloid angiopathy (CAA), and mild cognitive impairment (MCI). In one embodiment, the neurodegenerative disorder is selected from the group consisting of Alzheimer's disease, Pick's disease, corticobasal degeneration, progressive supranuclear palsy and frontotemporoparietal dementia. In one embodiment, the neurodegenerative disorder is selected from the group consisting of Alzheimer's disease, frontotemporal dementias, Parkinson's disease, and polyglutamine diseases, sporadic and familial Alzheimer's disease, Down's syndrome, progressive supranuclear palsy, Huntington's disease, sporadic and familial synucleinopathies, multiple system atrophy, neurogeneration with brain iron accumulation, neuronal intranuclear inclusion disease, hereditary spastic paraplegias, Charcot-Marie-Tooth disease, and sporadic and/or hereditary prion disease. In one embodiment, the neurodegenerative disorder is selected from the group consisting of a cognitive disorder, Alzheimer's disease, a neuro-degenerative disorder, age-related dementia, age-induced memory impairment, and movement disorder. In one embodiment, the neurodegenerative disorder is Alzheimer's disease. In one embodiment, the symptoms of the neurodegenerative disorder is selected from the group consisting of cognitive deficits, memory impairment, movement disorders, and motor complications. In one embodiment, symptoms of the Alzheimer's disease disorder is selected from the group consisting of cognitive deficits, memory impairment, movement disorders, and motor complications.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof reduces phosphorylation of levels of at least one phosphorylation site of tau protein in the nervous system of the subject.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof inhibits or prevents phosphorylation of at least one phosphorylation site on tau protein having a plurality of phosphorylation sites, wherein the tau protein is in the nervous system of the subject.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof reduces the amount of phosphorylated tau protein in the nervous system of the subject.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt inhibits or prevents phosphorylation of at least one phosphorylation site on tau protein having a plurality of phosphorylation sites, wherein the tau protein is in the nervous system of the subject.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof results in decreased amount of phosphorylated tau protein in the nervous system of the subject compared to the amount of phosphorylated tau protein in the nervous system of a control subject receiving a placebo, or to whom the compound of Formula (1), (1a), or (1b) and/or a pharmaceutically acceptable salt thereof has not been administered.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof results in decreased phosphorylated sites of tau protein, wherein the tau protein has a plurality of phosphorylation sites, in the nervous system of the subject compared with the number of phosphorylated sites of tau protein in the nervous system of a control subject receiving a placebo, or to whom the compound of Formula (1), (1a), or (1b) and/or a pharmaceutically acceptable salt thereof has not been administered.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof changes in lower level of phosphorylated tau protein in the nervous system of the subject compared to the level of phosphorylated tau protein in the nervous system of a control subject receiving the placebo, or to whom the compound of Formula (1), (1a), or (1b) and/or the pharmaceutically acceptable salt thereof has not been administered.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof reduces phosphorylation of levels of at least one phosphorylation site of tau protein in the brain of the subject.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof inhibits or prevents phosphorylation of at lest one phosphorylation site on tau protein having a plurality of phosphorylation sites, wherein the tau protein is in the brain of the subject.

In some embodiments, the methods of the present invention comprises administering a compound of Formula (1), (1a), or (1b) and/or the pharmaceutically acceptable salt thereof to a subject in need thereof, wherein the compound of Formula (1), (1a), or (1b) and/or the pharmaceutically acceptable salt thereof reduces the amount of phosphorylated tau protein in the brain of the subject.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt inhibits or prevents phosphorylation of at least one phosphorylation site on tau protein having a plurality of phosphorylation sites, wherein the tau protein is in the brain of the subject.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof results in decreased amount of phosphorylated tau protein in the brain of the subject compared to the amount of phosphorylated tau protein in the brain of a control subject receiving a placebo, or to whom the compound of Formula (1), (1a), or (1b) and/or a pharmaceutically acceptable salt thereof has not been administered.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof results in decreased phosphorylated sites of tau protein, wherein the tau protein has a plurality of phosphorylation sites, in the brain of the subject compared with the number of phosphorylated sites of tau protein in the brain of a control subject receiving a placebo, or to whom the compound of Formula (1), (1a), or (1b) and/or a pharmaceutically acceptable salt thereof has not been administered.

In some embodiments, the methods of the present invention comprises administering a compound of Formula (1), (1a), or (1b) and/or a pharmaceutically acceptable salt thereof to a subject in need thereof, wherein the compound of Formula (1), (1a), or (1b) and/or the pharmaceutically acceptable salt thereof changes in lower level of phosphorylated tau protein in the brain of the subject compared to the level of phosphorylated tau protein in the brain of a control subject receiving a placebo, or to whom the compound of Formula (1), (1a), or (1b) and/or a pharmaceutically acceptable salt thereof has not been administered.

In some embodiments, the methods of the present invention provide suitable combination therapy for treating and/or ameliorating symptoms of various neurodegenerative disorders. In one embodiment, a therapeutically effective amount of the compound of Formula (1), (1a), or (1b) and/or the pharmaceutically acceptable salt thereof is administered to the subject in need is administered in combination with a therapeutically effective amount of another pharmacological agent. In one embodiment, the pharmacological agents that would, in combination with the compounds of the present invention, be most effective in treating or ameliorating one or more symptoms of neurodegenerative disorders include cholinesterase inhibitors. In one embodiment, the pharmacological agents that would, in combination with the compounds of the present invention, be most effective in treating or ameliorating one or more symptoms of neurodegenerative disorders include selective serotonin re-uptake inhibitors (SSRIs) or serotonin-specific reuptake inhibitor. In one embodiment, the pharmacological agents that would, in combination with the compounds of the present invention, be most effective in treating or ameliorating one or more symptoms of neurodegenerative disorders include SSRIs selected from the group consisting of a citalopram (Celexa, Cipramil, Cipram, Dalsan, Recital, Emocal, Sepram, Seropram, Citox, Cital); dapoxetine (Priligy); escitalopram (Lexapro, Cipralex, Seroplex, Esertia); fluoxetine (Depex, Prozac, Fontex, Seromex, Seronil, Sarafem, Ladose, Motivest, Flutop, Fluctin (EUR), Fluox (NZ), Depress (UZB), Lovan (AUS), Prodep (IND)); fluvoxamine (Luvox, Fevarin, Faverin, Dumyrox, Favoxil, Movox, Floxyfral); indalpine (Upstene) (discontinued); paroxetine (Paxil, Seroxat, Sereupin, Aropax, Deroxat, Divarius, Rexetin, Xctanor, Paroxat, Loxamine, Deparoc); sertraline (Zoloft, Lustral, Serlain, Asentra, Tresleen); and zimelidine (Zelmind, Normud). In one embodiment, the pharmacological agents that would, in combination with the compounds of the present invention, be most effective in treating or ameliorating one or more symptoms of neurodegenerative disorders includes, but are not limited to, Razadyne, Exelon, Aricept, Cognex, and Namenda. In one embodiment, the pharmacological agents that would, in combination with the compounds of the present invention, be most effective in treating or ameliorating one or more symptoms of neurodegenerative disorders include, but are not limited to, Parcopa, Mirapex, Requip, Apokyn, Eldepryl, Zelapar, Azilect, Comtan, Tasmar, Cogentin, Sinemet, Neupro, Symmetrel, Selegiline, Rasagilene, Stalevo, Apokyn, Parlodel, and Artane. In one embodiment, the pharmacological agents that would, in combination with the compounds of the present invention, be most effective in treating or ameliorating one or more symptoms of neurodegenerative disorders include, but are not limited to, Zarontin, Felbatol, Gabitril, Keppra, Lamictal, Lyrica, Neurontin, Dilantin, Topamax, Trileptal, Depakene, Depakote, Zonegran, Valium, Ativan, Klonopin, Fycompa, and Oxtellar XR. In one embodiment, the pharmacological agents that would, in combination with the compounds of the present invention, be most effective in treating or ameliorating one or more symptoms of neurodegenerative disorders include, but are not limited to, Xenazine, Haldol Clozaril, Klonopin, Valium, Lexapro, Prozac, Sarafem, Zoloft, Lithobid, Depakene, Depakote, and Lamictal. In one embodiment, the pharmacological agents that would, in combination with the compounds of the present invention, be most effective in treating or ameliorating one or more symptoms of neurodegenerative disorders include, but are not limited to, Aricept, Reminyl, Exelon, Namenda, Risperdal, Zyprexa, and selective serotonin reuptake inhibitors (SSRIs). In one embodiment, the SSRIs are selected from the group consisting of Zimelidine, Celexa (citalopram), Lexopro, Luvox, Paxil (paroxetine), Prozac (fluoxetine), and Zoloft (sertraline). In one embodiment, the pharmacological agents that would, in combination with the compounds of the present invention, be most effective in treating or ameliorating one or more symptoms of neurodegenerative disorders include any neuroprotectant agent selective for NMDA subtype glutamate receptors in the central nervous system.

In one embodiment, when the neurodegenerative disorder is Alzheimer's disease, the compound of Formula (1), (1a), or (1b) and/or the pharmaceutically acceptable salt thereof can be administered to the subject in need thereof in combination with a therapeutically effective amount of Razadyne, Exelon, Aricept, Cognex, Namenda, or combinations thereof. In one embodiment, when the neurodegenerative disorder is Parkinson's disease, the compound of of Formula (1), (1a), or (1b) and/or the pharmaceutically acceptable salt thereof can be administered to the subject in need thereof in combination with a therapeutically effective amount of Parcopa, Mirapex, Requip, Apokyn, Eldepryl, Zelapar, Azilect, Comtan, Tasmar, Cogentin, Sinemet, Neupro, Symmetrel, Selegiline, Rasagilene, Stalevo, Apokyn, Parlodel, Artane, or combinations thereof. In one embodiment, when the neurodegenerative disorder is Seizure, the compound of Formula (1), (1a), or (1b) and/or the pharmaceutically acceptable salt thereof can be administered to the subject in need thereof in combination with a therapeutically effective amount of Zarontin, Felbatol, Gabitril, Keppra, Lamietal, Lyrica, Neurontin, Dilantin, Topamax, Trileptal, Depakene, Depakote, Zonegran, Valium, Ativan, Klonopin, Fycompa, Oxtellar XR, or combinations thereof. In one embodiment, when the neurodegenerative disorder is Huntington's Disease, the compound of Formula (1), (1a), or (1b) and/or the pharmaceutically acceptable salt thereof can be administered to the subject in need thereof in combination with a therapeutically effective amount of Xenazine, Haldol, Clozaril, Klonopin, Valium, Lexapro, Prozac, Sarafem, Zoloft, Lithobid, Depakene, Depakote, Lamictal, or combinations thereof. In one embodiment, when the neurodegenerative disorder is Supranuclear Palsy, the compound of Formula (1), (1a) or (1b) and/or the pharmaceutically acceptable salt thereof can be administered to the subject in need thereof in combination with a therapeutically effective amount of Parcopa, Mirapex, Requip, Apokyn, Eldepryl, Zelapar, Azilect, Comtan, Tasmar (rarely), Cogentin, Sinemet, Neupro, Symmetrel, Selegiline, Rasagilene, Stalevo, Apokyn, Parlodel, Artane, or combinations thereof. In one embodiment, when the neurodegenerative disorder is Dementia, the compound of Formula (1), (1a), or (1b) and/or the pharmaceutically acceptable salt thereof can be administered to the subject in need thereof in combination with a therapeutically effective amount of Aricept, Reminyl, Exelon, Namenda, Risperdal, Zyprexa, SSRIs, and combinations thereof. In one embodiment, when the neurodegenerative disorder is traumatic brain injury, the compound of Formula (1), (1a), or (1b) and/or the pharmaceutically acceptable salt thereof can be administered to the subject in need thereof in combination with a therapeutically effective amount of anti-depressants, pain medications, and combinations thereof. In one embodiment, when the neurodegenerative disorder is Down's Syndrome, the compound of Formula (1, (1a), or (1b) and/or the pharmaceutically acceptable salt thereof can be administered to the subject in need thereof in combination with age appropriate a stimulative at sensory, motor cognitive activities, and combinations thereof. In one embodiment, when the neurodegenerative disorder is a tauopathy, the compound of Formula (1), (1a), or (1b) and/or the pharmaceutically acceptable salt thereof can be administered to the subject in need thereof in combination with a therapeutically effective amount of Razadyne, Exelon, Aricept, Cognex (rarely), Namenda, Parcopa, Mirapex, Requip, Apokyn, Eldepryl, Zelapar, Azilect, Comtan, Tasmar (rarely), Cogentin, Sinemet, Neupro, Symmetrel, Selegiline, Rasagilene, Stalevo. Apokyn, Parlodel, Artane, or combinations thereof. In one embodiment when the neurodegenerative disorder is movement disorders, the compound of Formula (1), (1a), or (1b) and/or the pharmaceutically acceptable salt thereof can be administered to the subject in need thereof in combination with a therapeutically effective amount of Tetrabenazine (Xenazine), antipsychotic drugs, such as haloperidol (Haldol) and clozapine (Clozaril), clonazepam (Klonopin) and antianxiety drugs such as diazepam (Valium), Antidepressants include such drugs as escitalopram (Lexapro), fluoxetine (Prozac, Sarafem) and sertraline (Zoloft), Antipsychotic drugs, Mood-stabilizing drugs that can help prevent the highs and lows associated with bipolar disorder include lithium (Lithobid) and anticonvulsants, such as valproic acid (Depakene), divalproex (Depakote) and lamotrigine (Lamictal), Parcopa, Mirapex, Requip, Apokyn, Eldepryl, Zelapar, Azilect, Comtan, Tasmar (rarely), Cogentin, Sinemet, Neupro, Symmetrel, Selegiline, Rasagilene, Stalevo, Apokyrn, Parlodel, Artane, or combinations thereof.

In one embodiment, when the neurodegenerative disorder is memory impairment, the compound of Formula (1), (1a) or (1b) and/or the pharmaceutically acceptable salt thereof can be administered to the subject in need thereof in combination with a therapeutically effective amount of Razadyne, Exelon, Aricept, Cognex, Namenda or combinations thereof. In one embodiment, when the neurodegenerative disorder is cognitive disorder, the compound of Formula (1), (1a), or (1b) and/or the pharmaceutically acceptable salt thereof can be administered to the subject in need thereof in combination with a therapeutically effective amount of Razadyne, Exelon, Accept, Cognex, Namenda, or combinations thereof.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures, if any, and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

We claim:

1. A method of slowing down, preventing progression of, treating or ameliorating one or more symptoms of Alzheimer's disease, comprising parenterally administering to a subject in need thereof, a compound having a structure selected from Formula (1), Formula (1a), or Formula (1b):

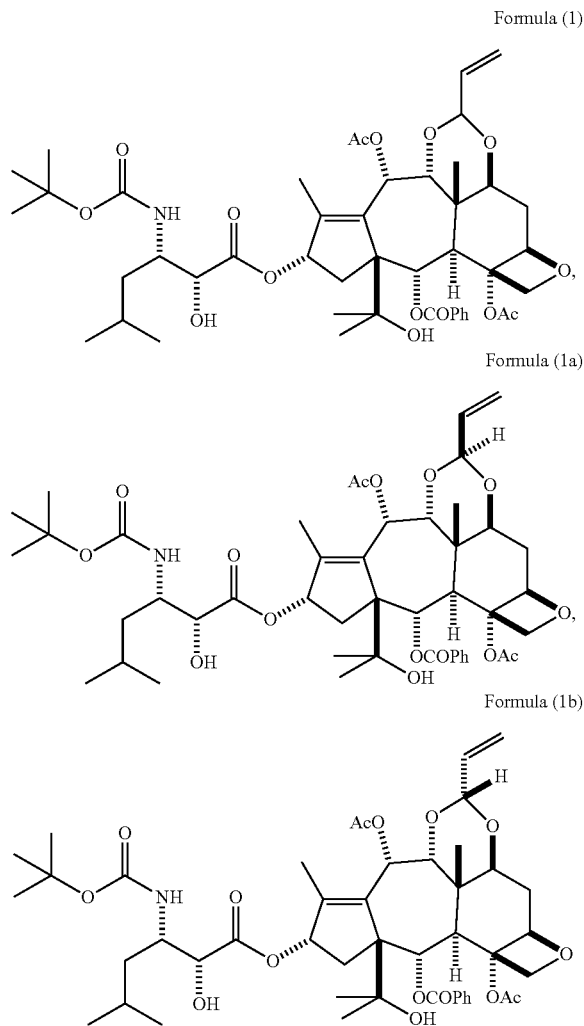

and/or a pharmaceutically acceptable salt thereof at a therapeutically effective dose ranging from about 0.001 mg/m$^2$ to about 20 mg/m$^2$.

2. The method of claim 1, wherein the compound of Formula (1), (1a), or 1(b) and/or the pharmaceutically acceptable salt thereof is administered in a single dose or in divided doses.

3. The method of claim 2, wherein the compound of Formula (1), (1a), or (1b), and/or the pharmaceutically acceptable salt thereof is administered in a single dose per day or in divided doses per day.

4. The method of claim 1, wherein the compound of Formula (1), (1a), or (1b) and/or the pharmaceutically acceptable salt thereof is administered at least once daily on alternative days.

5. The method of claim 1, wherein the compound of Formula (1), (1a), or (1b) and/or the pharmaceutically acceptable salt thereof is administered weekly.

6. The method of claim 5, wherein the compound of Formula (1), (1a), or (1b) and/or the pharmaceutically acceptable salt thereof is administered weekly divided into equal and/or unequal doses.

7. The method of claim 1, wherein the compound of Formula (1), (1a), or (1b) and/or the pharmaceutically acceptable salt thereof is administered once every three weeks.

8. The method of claim 1, wherein the compound of formula (1), (1a), or (1b) and/or the pharmaceutically acceptable salt thereof is administered monthly.

9. The method of claim 2, wherein the compound of Formula (1), (1a), or (1b), and/or the pharmaceutically acceptable salt thereof is administered in a single dose per month and/or in divided doses per month.

10. The method of claim 1, wherein the compound of Formula (1), (1a), or (1b) and/or the pharmaceutically acceptable salt thereof is administered at least once monthly for at least two successive months.

11. The method of claim 1, wherein the symptoms of Alzheimer's disease are selected from the group consisting of cognitive deficits, memory impairment, movement disorders, and motor complications.

12. The method of claim 1, wherein the compound of Formula (1), (1a), or (1b) and/or the pharmaceutically acceptable salt thereof is administered at a dose selected from the group consisting of from about 0.001 $mg/m^2$ to about 15 $mg/m^2$, from about 0.001 $mg/m^2$ to about 10 $mg/m^2$, and from about 0.001 $mg/m^2$ to about 5 $mg/m^2$.

13. The method of claim 1, wherein the compound of Formula (1), (1a), or (1b) and/or the pharmaceutically acceptable salt thereof is administered at a dose selected from the group consisting of about 0.1 $mg/m^2$, about 0.2 $mg/m^2$, about 0.3 $mg/m^2$, about 0.4 $mg/m^2$, about 0.5 $mg/m^2$, about 0.6 $mg/m^2$, about 0.7 $mg/m^2$, about 0.8 $mg/m^2$, about 0.9 $mg/m^2$, about 1.0 $mg/m^2$, about 1.1 $mg/m^2$, about 1.2 $mg/m^2$, about 1.3 $mg/m^2$, about 1.4 $mg/m^2$, about 1.5 $mg/m^2$, about 1.6 $mg/m^2$, about 1.7 $mg/m^2$, about 1.8 $mg/m^2$, about 1.9 $mg/m^2$, about 2 $mg/m^2$, about 2.1 $mg/m^2$, about 2.2 $mg/m^2$, about 2.3 $mg/m^2$, about 2.4 $mg/m^2$, about 2.5 $mg/m^2$, about 2.6 $mg/m^2$, about 2.7 $mg/m^2$, about 2.8 $mg/m^2$, about 2.9 $mg/m^2$, about 3 $mg/m^2$, about 3.1 $mg/m^2$, about 3.2 $mg/m^2$, about 3.3 $mg/m^2$, about 3.4 $mg/m^2$, about 3.5 $mg/m^2$, about 3.6 $mg/m^2$, about 3.7 $mg/m^2$, about 3.8 $mg/m^2$, about 3.9 $mg/m^2$, about 4 $mg/m^2$, about 4.1 $mg/m^2$, about 4.2 $mg/m^2$, about 4.3 $mg/m^2$, about 4.4 $mg/m^2$, about 4.5 $mg/m^2$, about 4.6 $mg/m^2$, about 4.7 $mg/m^2$, about 4.8 $mg/m^2$, about 4.9 $mg/m^2$, about 5 $mg/m^2$, about 5.1 $mg/m^2$, about 5.2 $mg/m^2$, about 5.3 $mg/m^2$, about 5.4 $mg/m^2$, about 5.5 $mg/m^2$, about 5.6 $mg/m^2$, about 5.7 $mg/m^2$, about 5.8 $mg/m^2$, about 5.9 $mg/m^2$, about 6 $mg/m^2$, about 6.1 $mg/m^2$, about 6.2 $mg/m^2$, about 6.3 $mg/m^2$, about 6.4 $mg/m^2$, about 6.5 $mg/m^2$, about 6.6 $mg/m^2$, about 6.7 $mg/m^2$, about 6.8 $mg/m^2$, about 6.9 $mg/m^2$, about 7 $mg/m^2$, about 7.1 $mg/m^2$, about 7.2 $mg/m^2$, about 7.3 $mg/m^2$, about 7.4 $mg/m^2$, about 7.5 $mg/m^2$, about 7.6 $mg/m^2$, about 7.7 $mg/m^2$, about 7.8 $mg/m^2$, about 7.9 $mg/m^2$, about 8 $mg/m^2$, about 8.1 $mg/m^2$, about 8.2 $mg/m^2$, about 8.3 $mg/m^2$, about 8.4 $mg/m^2$, about 8.5 $mg/m^2$, about 8.6 $mg/m^2$, about 8.7 $mg/m^2$, about 8.8 $mg/m^2$, about 8.9 $mg/m^2$, about 9 $mg/m^2$, about 9.1 $mg/m^2$, about 9.2 $mg/m^2$, about 9.3 $mg/m^2$, about 9.4 $mg/m^2$, about 9.5 $mg/m^2$, about 9.6 $mg/m^2$, about 9.7 $mg/m^2$, about 9.8 $mg/m^2$, about 9.9 $mg/m^2$, about 10 $mg/m^2$, about 11.0 $mg/m^2$, about 12.0 $mg/m^2$, about 13.0 $mg/m^2$, about 14.0 $mg/m^2$, about 15.0 $mg/m^2$, about 16.0 $mg/m^2$, about 17.0 $mg/m^2$, about 18.0 $mg/m^2$, about 19.0 $mg/m^2$, and about 20.0 $mg/m^2$.

* * * * *